United States Patent [19]

Picciola et al.

[11] Patent Number: 4,571,401
[45] Date of Patent: Feb. 18, 1986

[54] 3-PYRIDINE ACETIC AND 3-(3-PYRIDYL-METHOXYCARBONYL)-PROPIONIC ACID PANTETHEINE AND PANTETHEINE ESTERS HAVING HYPOLIPEMIC ACTIVITIES

[75] Inventors: Giampaolo Picciola, Milan; Piergiorgio Gentili, Treviglio; Franco Ravenna; Mario Riva, both of Monza, all of Italy

[73] Assignee: Maggioni Farmaceutici S.p.A., Milan, Italy

[21] Appl. No.: 629,512

[22] Filed: Jul. 10, 1984

[30] Foreign Application Priority Data

Jul. 19, 1983 [GB] United Kingdom ................ 8319457
Dec. 14, 1983 [GB] United Kingdom ................ 8333302

[51] Int. Cl.⁴ .................. C07D 213/55; C07D 401/12; C07D 401/14; A61K 31/44

[52] U.S. Cl. .................. 514/332; 546/255; 546/265; 546/291

[58] Field of Search ............... 546/255, 256, 291, 265; 514/332

[56] References Cited

U.S. PATENT DOCUMENTS 4,288,441 9/1981 Miki et al. ........................ 546/318

Primary Examiner—Alan L. Rotman
Attorney, Agent, or Firm—Oblon, Fisher, Spivak, McClelland & Maier

[57] ABSTRACT

The present invention relates to esters of pantetheine and pantethine with 3-pyridineacetic or 3-(3-pyridylmethoxycarbonyl)-propionic acid and to therapeutically acceptable acid addition salts thereof. The compounds show a high degree of hypolipemic activity.

8 Claims, 2 Drawing Figures

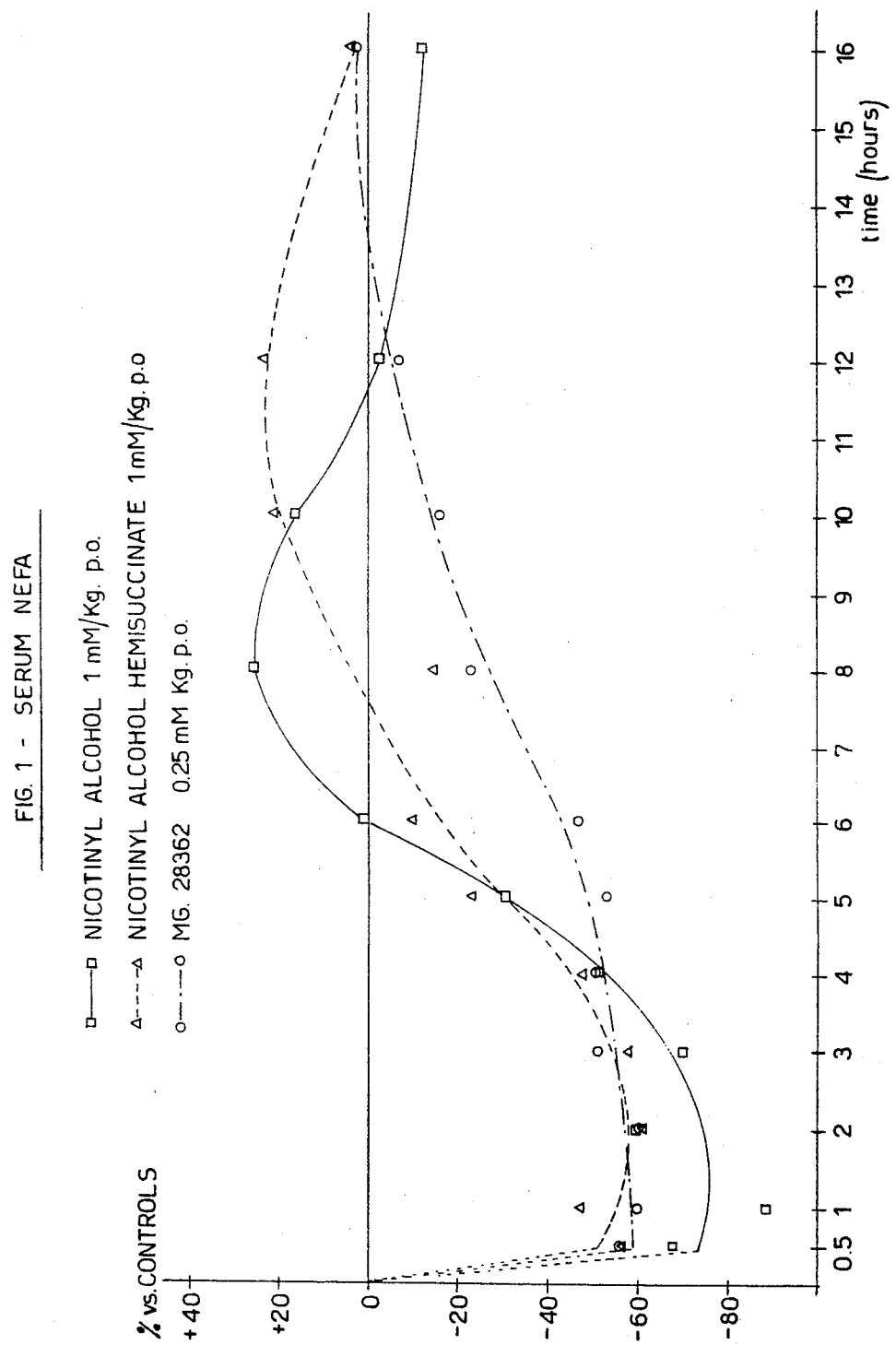

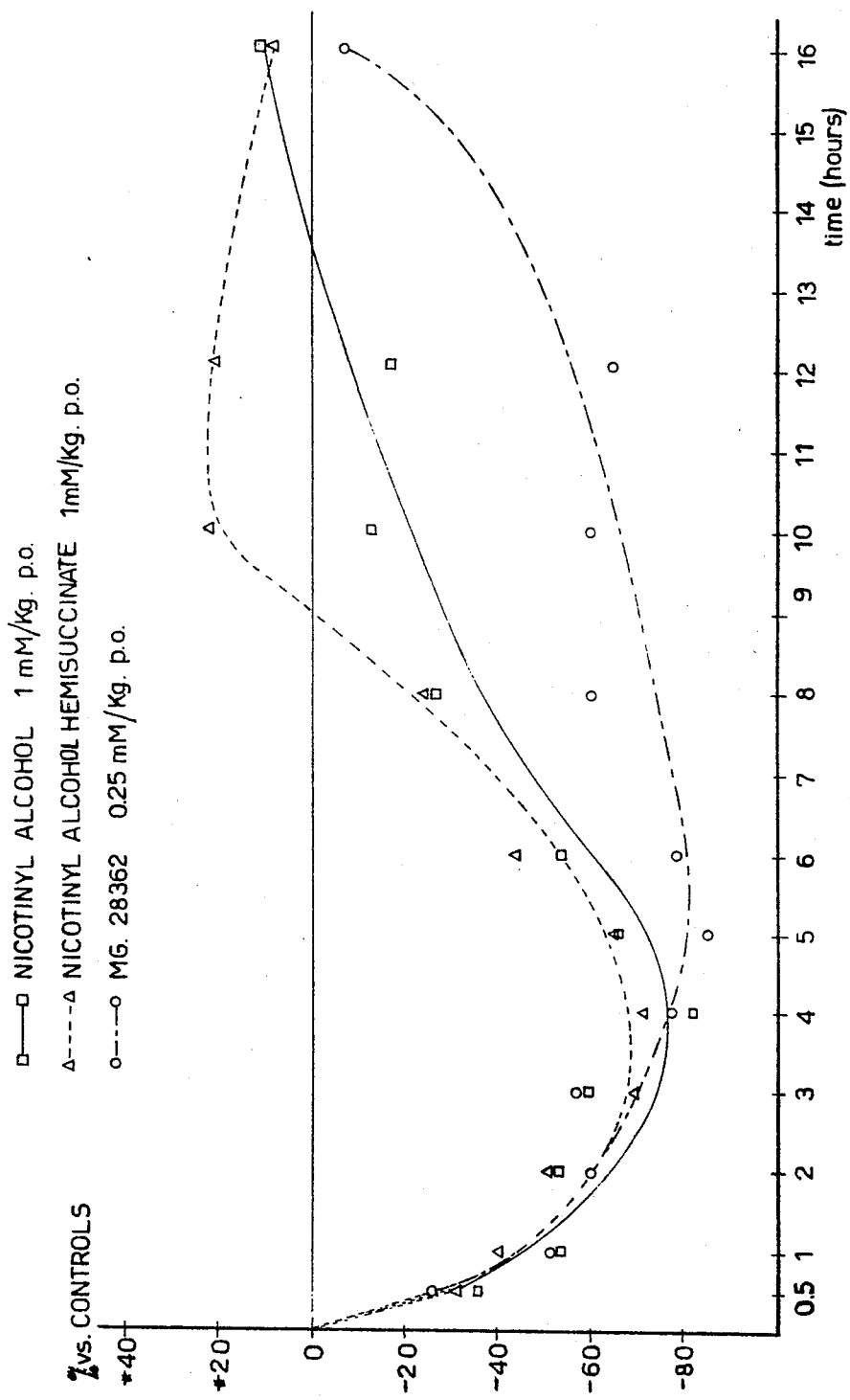

3-PYRIDINE ACETIC AND 3-(3-PYRIDYL-METHOXYCARBONYL)-PROPIONIC ACID PANTETHEINE AND PANTETHEINE ESTERS HAVING HYPOLIPEMIC ACTIVITIES

BACKGROUND OF THE INVENTION

1. Field of the Invention

The present invention relates to esters of pantetheine and pantethine with 3-pyridineacetic or 3-(3-pyridylmethoxycarbonyl)-propionic acid and to therapeutically acceptable acid addition salts thereof. The compounds show a high degree of long lasting hypolipemic activity devoid of undesirable side effects.

2. Description of the Prior Art

Nicotinoyl derivatives of pantethine and pantetheine with hypolipemic activity are known. For instance, Japanese published patent specification No. 80.102,566 discloses nicotinoylpantethines, while Japanese published patent specification No. 80.102,567 and U.S. Pat. No. 4,288,441 disclose nicotinoylpantetheines. However the need exists for compounds having more prolonged activity.

SUMMARY OF THE INVENTION

The present invention provides compounds exhibiting high and long lasting activity as hypocholesteremic agents without undesirable side effects.

These compounds are esters of 3-pyridyneacetic or 3-(3-pyridylmethoxycarbonyl)-propionic acid with pantetheine or pantethine, in which one or more of the available hydrogens of the hydroxy groups and (in the case of pantetheine) sulfhydryl group are replaced by acyl radicals deriving from the aforesaid carboxylic acids.

DETAILED DESCRIPTION OF THE INVENTION

This invention describes compounds having pharmacological activity. More particularly, the compounds with which this invention is concerned are represented by the following generic formula:

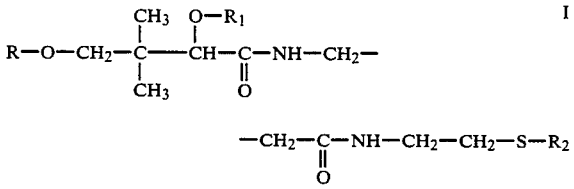

wherein R, $R_1$, and $R_2$ represent hydrogen or a 3-pyridineacetyl (II) or a 3-(3-pyridylmethoxycarbonyl)-propionyl (III) group

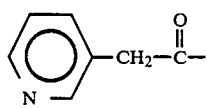

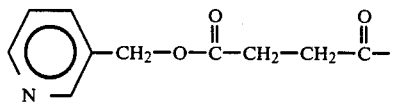

with the proviso that the three radicals R, $R_1$ and $R_2$ cannot represent simultaneously hydrogen; and moreover $R_2$ may also represent a group

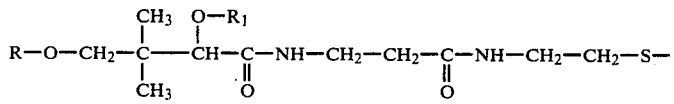

wherein the radicals R and $R_1$ have the above significance, with the proviso that for each individual compound the significance of R and $R_1$ will be the same as in formula I.

It will be apparent to those skilled in organic chemistry that the invention compounds are esterified derivatives of pantetheine or pantethine, depending whether the radical $R_2$ represents the above formula IV, and in this case the compounds will be pantethine derivatives with a disulfide group —S—S—, or the same radical $R_2$ represents hydrogen or one of the above radicals II and III, and in this case the compounds will be pantetheine derivatives.

The process for preparing the invention compounds consists in contacting pantetheine or pantethine with a molar excess of 3-pyridineacetic or 3-(3-pyridylmethoxycarbonyl)-propionic acid in an organic solvent in the presence of a catalyst of the condensation reaction and in the presence of an amount of a condensing agent approximately equivalent to the amount of acid used in the reaction, at a temperature ranging between about −15° C. and +25° C.

The amount of acid selected for introducing the radicals II and III will obviously vary depending on the number of these radicals which are to be introduced into the pantetheine or pantethine molecule.

For instance, if the compound of formula I is desired in which R is one of the radicals II or III, $R_1$ is hydrogen and $R_2$ is the radical IV, at least two moles of the acid must be present. The same applies if both R and $R_1$ represent one of the radicals II and/or III and $R_2$ represents hydrogen. If, on the other hand, the compound is desired in which R and $R_1$ and $R_2$ all represent one of the radicals II or III, at least some excess over three moles for each mole of the starting compound (which obviously will be pantetheine) must be present.

The organic solvent in which the reaction is carried out is not critical, provided it does not interfere with the reaction. Solvents such as methylene chloride, chloroform, ethyl acetate, tetrahydrofuran, dioxane, diethyl ether, dimethylformamide, acetone, benzene have been found convenient, with some preference for methylene chloride. Alternatively, the reaction may be carried out using pyridine as the solvent; in this case it is preferred to add a catalytic amount of p-toluenesulfonic acid in order to prevent the concomitant formation of N-acylureas (Acta Chem. Scandinavica B 33 410, 1979).

The amount of solvent is not critical, and may be adjusted depending on the circumstances and the mass of the employed reactants. The catalyst of the condensation reaction may be an aliphatic, preferably tertiary, amine or a cyclic amine. As catalyst, a trialkylamine such as trimethyl- or triethylamine, a substituted pyridine such as a dialkylaminopyridine, e.g. 4-dimethyl- or 4-diethylaminopyridine; or 4-(1-pyrrolidino)-pyridine were found useful. Preferably 4-dimethyl or 4-diethylaminopyridine are used.

As above stated, the reaction temperature may range between $-15°$ C. and $+25°$ C. Preferably in most cases this temperature will be around $0°$ C., and more preferably between $-15°$ C. and $0°$ C.

As stated above, the reaction requires the presence of a condensing agent. This is preferably a carbodiimide; particularly useful was found to be dicyclohexylcarbodiimide.

The reaction time is not critical and may vary widely depending on the reactivity of the reactants, the selected temperature and the amount of solvent. Generally a reaction time from 3 to 40 hours was found convenient, more preferably from 6 to 24 hours.

The recovery of the end product from the reaction mixture is carried out according to procedures well known to the experts in the art.

Since the product is in solution in the process of solid substances, after filtration from the solids the solvent is removed, and for its purification the compound is preferably dissolved in a solvent or a solvent mixture and purified by chromatography. The eluate is then evaporated to dryness yielding the end product in a satisfactory purity condition.

The compounds of this invention may give addition salts with organic and inorganic acids. Useful organic acids are, e.g., carboxylic or sulfonic acids, and may contain other functional groups such as for instance hydroxy, amino, etc. Useful organic acids are the following: formic, acetic, propionic, glycolic, lactic, citric, ascorbic, fumaric, maleic, oxalic, pamoic, succinic, tartaric, phenylacetic, benzoic, p-aminobenzoic, anthranilic, p-hydroxybenzoic, salicylic, malic, methanesulfonic, ethanedisulfonic, glucuronic, glutamic acids and others. Useful inorganic acids are for instance hydrochloric, hydrobromic, hydroiodic, sulfuric, phosphoric, perchloric acids and others. The compounds of this invention were highly active as hypolipemics and platelet aggregation inhibitors.

For determining the hypolipemic activity the following procedures were carried out:
Triton hyperlipemia;
Ethanol hypertriglyceridemia;
Diet hypercholesteremia.

As far as the first test is concerned, the procedure was the one described by A. Arnold et al, J. Pharmac. Sci. 68 1557 (1979).

The results obtained are reported in Table I. They show that the compound of Example 3, having formula VII, hereinafter referred to as compound MG-28,362, displays a hypolipemic effect higher than the two comparison substances, i.e. nicotinyl alcohol and nicotinyl alcohol hemisuccinate. Actually MG-28,362 decreases the total cholesterol, the triglycerides, the total lipids and phospholipids in plasma while causing a moderate increase of HDL cholesterol. On the contrary the effect due to nicotinyl alcohol and nicotinyl hemisuccinate was much lower and the reductions were not statistically significant, while HDL cholesterol was slightly decreased. In addition liver cholesterol and triglycerides were more markedly reduced after treatment with MG-28,362.

TABLE I

| | Triton Test - Percent Decrease with Respect to Control | | | | | | |
|---|---|---|---|---|---|---|---|
| Treatment (mM/kg per os) | Cholesterol mg % | Triglycerides mg % | HDL-Chol. mg % | Total lipids mg % | Phospholipids mg % | Liver cholesterol mg/g | Liver triglycerides mg/g |
| Triton + H 0 | 247.44 ± ±17.84 | 1242.75 ±194.02 | 34.19 ±3.45 | 1979.19 ±239.05 | 338.88 ±34.14 | 11.67 ±0.58 | 21.80 ±1.67 |
| Triton + NA 1 | −18.4 | −7.7 | −9.6 | −13.4 | −15.5 | −23 | −25.9 |
| Triton + NA 4 | −13.5 | −15.3 | −22.4 | −16.3 | −2.5 | −20.5 | −13.5 |
| Triton + NAH 4 | −22.2 | −36.2 | −12.8 | −23.7 | −18.4 | −21.1 | −31.7 |
| Triton + MG 28,362 0.25 | −35.6 | −50 | +12.6 | −34.1 | −27.9 | −28.8 | −41 |
| Triton + MG 28,362 1 | −37.7 | −64.2 | −6.7 | −48.3 | −34.4 | −35.1 | −44.7 |

NA = Nicotinyl Alcohol
NAH = Nicotinyl Alcohol Hemisuccinate

Hypertriglyceridemia from ethanol was determined by the procedure of C. R. Sirtori et al., Atherosclerosis 30 45 (1978). From the data reported in Table II it is noted that ethanol administration causes an apparent increase of plasma triglycerides in animals treated with the solvent alone. The increase is inhibited by MG-28,362 in a more gradual and durable way than by the two comparison substances.

TABLE II

| | Ethanol Hypertriglyceridemia Percent Decrease with Respect to Controls | | | | |
|---|---|---|---|---|---|
| Treatment mM/Kg per os | 4 hrs | 6 hrs | 12 hrs | 16 hrs | 24 hrs |
| Ethanol + H$_2$O | 466.51$^x$ ±52.19 | 313.86$^x$ ±17.63 | 315.11$^x$ ±28.33 | 340.00$^x$ ±41.23 | 227.19$^x$ ±19.74 |
| Ethanol + NA 1 | −36.7 | −52.4 | −26.8 | −5.2 | +38.7 |
| Ethanol + NAH 1 | — | −38.5 | −27.6 | −16.4 | +51.4 |
| Ethanol + MG-28,362 0.25 | −35.5 | −32.0 | −52.8 | −48.2 | +18.5 |

$^x$ = serum triglycerides (mg %)
NA = Nicotinyl Alcohol
NAH = Nicotinyl Alcohol Hemisuccinate Diet hypercholesteremia was determined by the procedure of Nath et al., J. Nutrition 67 289 (1959). The data reported in Table III show that MG-28,362 displays also in this test a hypolipemic activity higher than nicotinyl alcohol. In fact MG-28,362 reduced in a more marked way the total cholesterol, total lipids and phospholipids in serum and caused a remarkable increase (+39.2%) of HDL-cholesterol. Moreover, unlike nicotinyl alcohol, MG-28,362 reduced also liver cholesterol and did not cause triglyceride accumulation in liver.

TABLE III

Nath Diet Hypercholesteremia
Percent Decrease with Respect to Controls

| Treatment (mM/Kg per os) | Cholesterol mg % | Triglycerides mg % | HDL-Chol. mg % | Total lipids mg % | Phospholipids mg % | Liver Cholesterol mg/g | Liver Triglycerides mg/g |
|---|---|---|---|---|---|---|---|
| NATH + H 0 | 279.43 +29.17 | 96.15 +8.92 | 28.24 +1.45 | 728.28 +56.29 | 163.94 +10.83 | 31.44 +2.57 | 35.97 +2.46 |
| NATH + NA 1 | −19.9 | +24.8 | +19.6 | −3.6 | −6.5 | +3.4 | +15.6 |
| NATH + NA 4 | −32.8 | +43.1 | +16.7 | — | −18.8 | −1.7 | +30.4 |
| NATH + MG-28,362 0.25 | −38.0 | +23.2 | +0.3 | −31.5 | −28.2 | −5.6 | +5.4 |
| NATH + MG-28,362 1 | −43.0 | −6.8 | +39.2 | — | −29.7 | −29.3 | −13.5 |

NATH = Nath Diet
NA = Nicotinyl Alcohol.

By another procedure, groups of 6 rats CrI:CD(SD)BR weighing 180 g were treated orally with the same doses of the same substances of the preceding experiment. The animals were sacrificed at different times after the single treatment (at 30, 60, 120, 180, 240, 300, 360, 480, 600, 720 and 960 minutes) and in their blood the non-esterified fatty acids (NEFA) were determined. Treatment with MG-28,362 caused a decrease of plasma NEFA more persistent that the decrease caused by nicotinyl alcohol (NA) or nicotinyl alcohol hemisuccinate (NAH). The NEFA decrease caused by NA and NAH was exhausted after about 6 hours and was followed by rebound with increase of NEFA by about 25%. The effect caused by MG-28,362 was more durable (10–12 hours) and no rebound occurred. FIG. 1 is representative of the experimental results The same test, as showed in FIG. 2, indicates that the plasma triglyceride decrease following treatment with MG-28,362 was more durable (about 16 hrs) than with NAH(8–9 hrs). Also in this case, after the NAH effect was over, triglycerides increase by about 20% (rebound) was observed.

The platelet aggregation inhibiting activity was determined by the procedure of D. H. Minsker et al., J. Pharmacol. Exp. Ther. 210 37 (1979) with minor modifications.

Table IV gives the percent decrease of maximum aggregation and aggregation rate observed on treated animals as compared with controls. MG-28,362 caused an apparent inhibition of platelet aggregation both after 1 and after 4 hours from administration.

MG-28,362 therefore displays an activity more prolonged than pantethine which is active after 1 hr but inactive after 4 hrs. Nicotinyl alcohol was totally inactive after both considered times.

TABLE IV

Platelet Aggregation Inhibition ex vivo against Collagen

| Substance and doses (mM/Kg per os) | Pretreatment (hrs) | % decrease of maximum aggregation (m + ES) | % decrease of aggregation rate (m + ES) |
|---|---|---|---|
| MG-28,362 1.8 | 1 | −66.6 ± 18.6 | −62.8 ± 18.4 |
| 1.8 | 4 | −77.0 ± 12.8 | −71.9 ± 13.7 |
| Pantethine 1.8 | 1 | −65.7 ± 14.4 | −67.0 ± 13.6 |
| 1.8 | 4 | −15.2 ± 3.2 NS | −24.7 ± 12.1 NS |
| Nicotinyl 7.2 | 1 | −28.6 ± 15.0 NS | −24.3 ± 10.6 NS |
| alcohol 7.2 | 4 | −8.8 ± 3.0 NS | −12.8 ± 5.6 NS |

NS = Not Significative with respect to controls.
Each experiment was made on blood pool of 3 treated and 3 control rats.
Five experiments were made for each test.

After administration of MG-28,362 and of the compound of Example 1 (MG-28,356) in high doses no cutaneous flush was noted, an undesirable side effect occurring after ingestion of low doses of nicotinic acid and nicotinyl alcohol. This property was determined by the procedure of G. G. Andersson et al., Acta Pharmacol. Toxicol 41 1 (1977). Actually, nicotinyl alcohol, in a dosis of 30.5 μM/Kg, caused an apparent skin flushing and a sudden rise (+6.5° C.) of ear skin temperature.

This effect was over in about 40 minutes. On the contrary, administration of MG-28,362 in doses of 60.9 and 121.8 μM/Kg, doses containing 8 and 16 times higher amounts of nicotinyl alcohol, did not cause skin flushing and did not apparently modify ear skin temperature.

The analysis of behavior according to Irwin showed that the invention compounds do not cause significant behavior modification at doses of 1000–2000 mg/kg orally.

The invention compounds also show a very low acute toxicity. Doses of 1000–2000–4000 mg/kg orally and intraperitoneally in mica CrI:CD-1(ICR)BR of both sexes did not cause any death or apparent toxic symptoms. The $LD_{50}$ was therefore higher than 4000 mg/kg. All the foregoing tests were carried out using L(+)tartaric acid in order to solubilize the compounds. Doses were calculated with respect to the base.

The compounds of this invention and their pharmacologically acceptable acid addition salts may be administered to humans in conventional pharmaceutical dosage unit forms, such as capsules, tablets, powders, elixirs for oral route, or alternatively as parenterally administrable solutions, using common excipients, solvents, diluents, preservatives etc. Indicative single doses may range between 0.05 and 2.0 g, with daily dosages ranging between 0.1 and 10.0 g. All these figures are with respect to the free bases to which one must make reference when using acid addition salts of the compounds.

The following Examples are illustrative of this invention but they are not intended to establish its limits.

EXAMPLE 1

To a suspension of 10 g of 3-pyridineacetic acid (0.07292 mole) in 200 ml of methylene chloride, 9.63 g of pantethine (0.01736 mole) and 0.850 g of 4-dimethylaminopyridine (0.00695 mole) are added under stirring. The suspension is cooled to −5° C. and at this temperature 14.68 g of dicyclohexylcarbodiimide (0.07118 mole) are added. The reaction mixture is allowed to stand under stirring for 3 hrs at 0° C. and for additional 21 hrs at 25° C. The solids are filtered off and the filtrate is washed with a 5 percent aqueous solution of sodium carbonate and then with water. The organic layer is dried over sodium sulfate and the solvent is distilled off. 16.5 g of a residue are obtained, which are eluted with a chloroform:methanol (9:1) mixture through a chromatographic column containing 660 g Merck silicagel 60 (70–230 mesh). After concentration under reduced pressure, 10 g of compound of formula V are obtained (yield 55.9%), which appears as a foamy, slightly hygroscopic solid.

In the $^{13}$C-NMR spectrum (300 MHz) (CDCl$_3$) the following signals are found (in ppm)

| | |
|---|---|
| Four kinds of C=O (c, f, l, s) | 172.09 |
| values in accordance with the | 170.32 |
| chemical shifts of amides and | 169.73 |
| esters) | 167.71 |
| Four kinds of C in alpha to the | 150.50 (d) |
| pyridinic N (o, r, v, y) | 150.40 (d) |
| | 148.65 (d) |
| | 148.51 (d) |
| Two kinds of C in gamma to pyridinic | 137.13 (d) |
| N (p, w) | 137.02 (d) |
| Two kinds of quaternary C pyridine ring (n, u) | 129.87 (s) |
| | 129.46 (s) |
| two kinds in C in beta to pyridine-N (q, x) | 123.58 (d) |
| | 123.54 (d) |
| CH—O (g) | 77.63 (d) |
| CH$_2$—O (k) | 69.88 (t) |
| six kinds of CH$_2$ (a, b, d, e, m, t) | 38.60 |
| | 38.39 |
| | 38.16 |
| | 38.05 |
| | 35.67 |
| | 35.03 |
| quaternary C (h) | 37.49 (s) |
| CH$_3$ (i, j) | 21.37 |
| | 20.81 |

The multiplicity of signals was determined by the

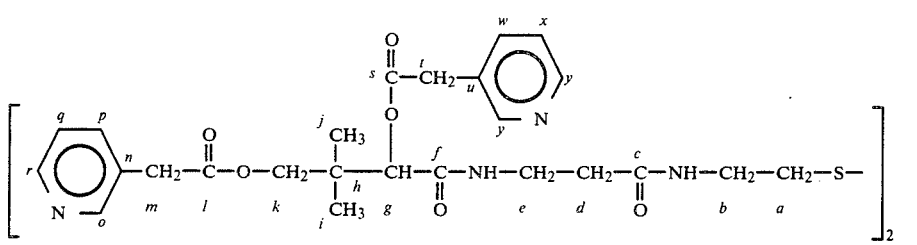

V

The compound is unitary at TLC (eluent CHCl$_3$:CH$_3$OH 9:1) and at HPLC.

$[\alpha]_D^{25} = +43.9°$ (c=1 in CH$_3$OH)

Elemental analysis (C$_{50}$H$_{62}$N$_8$O$_{12}$S$_2$):

| | | | | |
|---|---|---|---|---|
| calc, % | C 58.23 | H 6.06 | N 10.87 | S 6.22 |
| found % | C 58.07 | H 6.09 | N 10.70 | S 6.14 |

In the $^1$H-NMR Spectrum(90 MHz) (CDCl$_3$, TMS) the following signals are found (in ppm)

| | | |
|---|---|---|
| CH$_3$ (i) + CH$_3$ (j) | (12H) | 0.90 (s) and 0.97 (s) |
| CH$_2$ (d) | (4H) | 2.36 (t) |
| CH$_2$ (a) | (4H) | 2.74 (t) |
| CH$_2$ (b) + CH$_2$ (e) | (8H) | 3.45 (m) |
| CH$_2$ (m) + CH$_2$ (t) | (8H) | 3.60 (s) and 3.74 (s) |
| CH$_2$—O (k) | (4H) | 3.8 (d) and 4.01 (d) $J_{gem} = 12$ Hz |
| CH—O (g) | (2H) | 4.84 (s) |
| NH + H (x,q) | (8H) | 7.3 (m) |
| H (p,w) | (4H) | 7.64 (m) |
| H (o,r,v,y) | (8H) | 8.5 (m) | off-resonance technique.

EXAMPLE 2

To a suspension of 5 g of 3-pyridineacetic acid (0.03646 mole) in 120 ml of methylene chloride, 9.19 g of pantethine (0.01657 mole) and 0.405 g of 4-dimethylaminopyridine (0.00331 mole) are added under stirring. The suspension is cooled to −5° C. and at this temperature 7.18 g of dicyclohexylcarbodiimide (0.03479 mole) are added. The reaction mixture is left under stirring for 3 hrs at 0° C. and for 21 hrs at 25° C.

The precipitate is filtered off and the filtrate is washed with a saturated aqueous solution of sodium carbonate and then with a saturated aqueous solution of sodium chloride. The organic layer is dried over sodium sulfate and evaporated to dryness. 8.1 g of residue are obtained, which is eluted with a chloroform:methanol (9:1) mixture through a chromatographic column containing 340 g of Merck silicagel 60 (70–230 mesh).

After concentration of the solution under reduced pressure, 5.4 g of compound VI are obtained (yield 41%) as a semi-solid oil of vitreous appearance

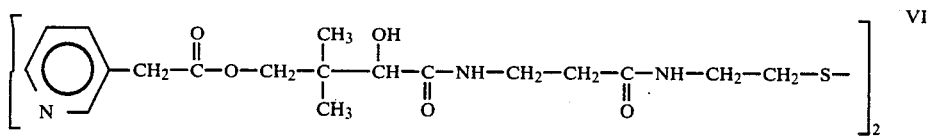

The compound is unitary at TLC (eluent CHCl$_3$:CH$_3$OH 9:1) and at HPLC.

Elemental analysis (C$_{36}$H$_{52}$N$_6$O$_{10}$S$_2$):

|  |  |  |  |  |
|---|---|---|---|---|
| calc. % | C 54.53 | H 6.61 | N 10.6 | S 8.08 |
| found % | C 54.33 | H 6.65 | N 10.43 | S 8.12 |

EXAMPLE 3

To a suspension of 15 g of 3-(3-pyridylmethoxycarbonyl)-propionic acid) in 300 ml of methylene chloride; 9.47 g of pantethine (0.01707 mole) and 0.835 g of 4-dimethylaminopyridine (0.00683 mole) are added under stirring. The suspension is cooled to −5° C. and at this temperature 14.44 g of dicyclohexylcarbodiimide (0.06999 mole) are added. The reaction mixture is left under stirring for 3 hrs at 0° C. and for 21 hrs at 25° C.

The precipitate is filtered off and the filtrate is washed with a 5% aqueous solution of sodium carbonate and then with water.

The organic layer is dried over sodium sulfate and evaporated to dryness. 20 g of residue are obtained, which are eluted with a chloroform:methanol (9:1) mixture through a chromatographic column containing 800 g of Merck silicagel 60 (70–230 mesh).

After concentration under reduced pressure of the solution, 13 g of compund VII are obtained (yield 57.7%).

-continued

| CH$_2$—O (k) | (4H) | 3.83 (d) and 4.04 (d) J$_{gem}$ = 12 Hz |
|---|---|---|
| CH—O (g) | (2H) | 4.88 (s) |
| CH$_2$—O (p) + CH$_2$—O (z) | (8H): | 5.17 (s) |
| NH + H (t,t') | (8H) | 7.2 (m) |
| H (s,s') | (4H) | 7.7 (m) |
| H (u, r, u', r') | (8H) | 8.6 (m) |

In the $^{13}$C-NMR spectrum (300 MHz) the following signals are found (in ppm)

| | |
|---|---|
| Six kinds of C=O (c, f, l, o, v, y) | 172.20 |
| (values in agreement with the | 172.02 |
| chemical shifts of amides and | 171.87 |
| esters) | 171.81 |
| | 171.18 |
| | 168.07 |
| C in alpha to pyridine-N (u, r, u', r') | 149.68 (d,d) |
| | 149.63 (d,d) |
| C in gamma to pyridine-N (s, s') | 136.03 (d) |
| | 136.00 (d) |
| quaternary pyridinic C (q, q') | 131.66 (s) |
| | 131.54 (s) |
| C in beta to pyridine-N (t, t') | 123.55 (d) |
| | 123.50 (d) |
| CH—O (g) | 77.58 (d) |
| CH$_2$—O (k) | 69.72 (t) |
| CH$_2$—O (p, z) | 64.26 (t) |
| | 64.07 (t) |
| CH$_2$ (a, b, d, e, m, n, w, x) | 38.62 (t) |
| | 38.05 (t) |

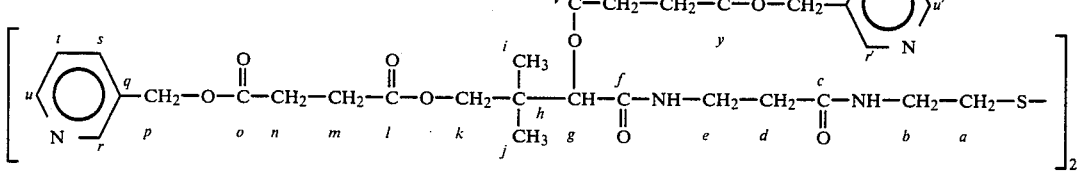

The substance is a semi-solid oil of vitreous appearance. It is unitary at TLC (eluent CHCl$_3$:CH$_3$OH 9:1) and at HPLC.

$[\alpha]_D^{25} = +13.4°$ (c=1 in CH$_3$OH)

Elemental analysis (C$_{62}$H$_{78}$N$_8$O$_{20}$S$_2$):

|  |  |  |  |  |
|---|---|---|---|---|
| calc. % | C 56.43 | H 5.96 | N 8.49 | S 4.86 |
| found % | C 56.23 | H 5.99 | N 8.53 | S 4.79 |

In the $^1$H-NMR spectrum (90 MHz) (CDCl$_3$, TMS) the following signals are found (in ppm)

| | | |
|---|---|---|
| CH$_3$ (i) + CH$_3$ (j) | (12H) | 0.99 (s) and 1.04 (s) |
| CH$_2$ (d) | (4H) | 2.42 (t) |
| CH$_2$ (m) + CH$_2$ (n) + CH$_2$ (w) + CH$_2$ (x) | (16H) | 2.7 (m) |
| CH$_2$ (a) | (4H) | 2.77 (t) |
| CH$_2$ (b) + CH$_2$ (e) | (8H) | 3.48 (m) |

| | |
|---|---|
| | 35.75 (t) |
| | 35.52 (t) |
| | 29.16 (t, t, t, t) |
| quaternary C (h) | 37.43 (s) |
| CH$_3$ (i, j) | 21.47 (q) |
| | 20.94 (q) |

The multiplicity of signals was determined by the off-resonance technique.

EXAMPLE 4

To a suspension of 5 g of 3-(3-pyridylmethoxycarbonyl)-propionic acid (0.0239 mole) in 120 ml of methylene chloride, 6.03 g of pantethine (0.01086 mole) and 0.265 g of 4-dimethylaminopyridine (0.00217 mole) are added under stirring. The suspension is cooled to −5° C. and at this temperature 4.71 g of dicyclohexylcarbodiimide (0.0228 mole) are added under stirring. The reaction mixture is left under stirring for 3 hrs at 0° C. and for 21 hrs at 25° C.

The precipitate is filtered off and the filtrate is washed with a saturated aqueous solution of sodium carbonate and then with a saturated aqueous solution of sodium chloride. The organic layer is dried over sodium sulfate and evaporated to dryness. 7.5 g of residue are obtained, which are eluted with a chloroform:methanol (9:1) mixture through a chromatographic column of Merck silicagel 60 (70–230 mesh)

After concentration under reduced pressure of the solution, 4.42 g of compound VIII are obtained (yield 43.4%). The substance is a semi-solid oil of vitreous appearance. It is unitary at TLC (eluent CHCl$_3$:CH$_3$OH 9:1) and at HPLC.

Elemental analysis (C$_{42}$H$_{60}$N$_6$O$_{14}$S$_2$):

| | | | | |
|---|---|---|---|---|
| calc. % | C 53.83 | H 6.45 | N 8.97 | S 6.84 |
| found % | 53.63 | H 6.53 | N 8.75 | S 6.63 |

| | | | | |
|---|---|---|---|---|
| calc. % | C 60.45 | H 5.86 | N 11.02 | S 5.04 |
| found % | C 60.30 | H 5.89 | N 11.05 | S 4.99 |

EXAMPLE 6

To a solution of 3.13 g of 3-pyridineacetic acid (0.0228 mole) and 3.08 g of 1-hydroxybenzotriazole (0.0228 mole) in 170 ml of anhydrous tetrahydrofuran, 4.70 g of dicyclohexylcarbodiimide (0.0228 mole) are added at 0° C. After 1 hr at 0° C. the precipitate is filtered off and to the filtrate 11 g of thallium (I) pantetheinate (0.0228 mole) are added at 25° C. and the reaction mixture is stirred at room temperature for 1.5 hrs.

The precipitate is filtered off and washed with tetrahydrofuran. The combined organic fluids are evaporated and the residue is dissolved in saline water and extracted with chloroform. The organic layer is washed

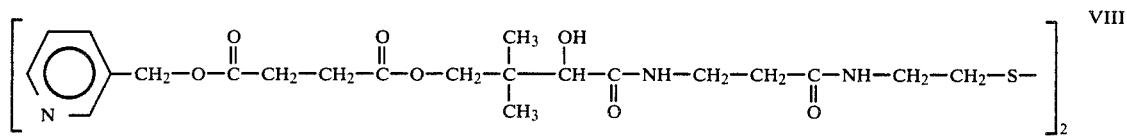

VIII

EXAMPLE 5

To a suspension of 3.83 g of pantetheine (0.0137 mole), 5.94 g of 3-pyridineacetic acid (0.0433 mole) and 0.5 g of 4-dimethylaminopyridine (0.0041 mole) in 80 ml of anhydrous methylene chloride, 8.79 g of dicyclohexylcarbodiimide (0.0426 mole) in 60 ml of anhydrous methylene cloride are added dropwise at −5° C. under a nitrogen atmosphere. The reaction mixture is stirred at room temperature for 20 hrs, then the precipitate is filtered off and washed with anhydrous methylene chloride. The combined organic filtrate and washings are washed with aqueous sodium bicarbonate, water and dried over sodium sulfate. After distilling off the solvent an oil is obtained (10.1 g) which is eluted with a chloroform:methanol (9:1) mixture through a chromatographic column containing 410 g of Merck silicagel 60 (70–230 mesh.)

After concentration under reduced pressure, 5 g of compound of formula IX are obtained (yield 57%) as a viscous oil.

with saline water, dried over sodium sulfate and evaporated to dryness. The residual oil (8 g) is eluted through a chromatographic column filled with 320 g of Merck silicagel 60 (70–230 mesh) with a chloroform:methanol (93:7) mixture. After concentration under reduced pressure 4.2 g (yield 46%) of an oily product are obtained of formula X.

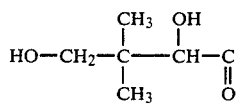 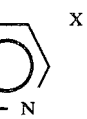

X

The compound is unitary at TLC (eluent CHCl$_3$:CH$_3$OH 85:15) and at HPLC.

Elemental analysis (C$_{18}$H$_{27}$N$_3$O$_5$S)

| | | | | |
|---|---|---|---|---|
| calc. % | C 54.39 | H 6.85 | N 10.57 | S 8.06 |
| found % | C 54.33 | H 6.89 | N 10.50 | S 8.00 |

EXAMPLE 7

To a suspension of 3.17 g of pantetheine (0,0114 mole), 7.5 g of 3-(3-pyridylmethoxycarbonyl)-propionic acid (0.0358 mole) and 0.42 g of 4-dimethylaminopyridine (0.0034 mole) in 70 ml of anhydrous methylene chloride, 7.28 g of dicyclohexylcarbodiimide (0.0353 mole) dissolved in 50 ml of anhydrous methylene chloride were added dropwise at −5° C. under a nitrogen atmosphere. The reaction mixture is stirred for 18 hrs at

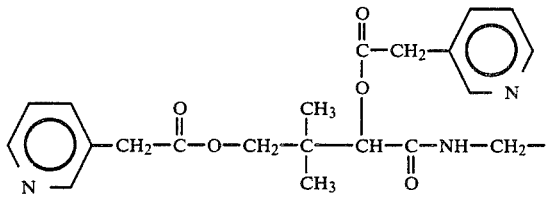

IX

The compound is unitary at TLC (eluent CHCl$_3$:CH$_3$OH 85:15) and at HPLC.

Elemental analysis (C$_{32}$H$_{37}$N$_5$O$_7$S):

room temperature. The precipitate is filtered off and washed with methylene chloride. The combined organic fluids are washed with aqueous sodium bicarbonate, water and then dried over sodium sulfate. The solvent is evaporated leaving an oily residue (12 g) which is eluted with a chloroform:methanol (93:7) mixture through a chromatographic column filled with 500 g of Merck silicagel 60 (70–230 mesh). After concentration under reduced pressure, 7.6 g (yield 78%) of an oily residue are obtained of formula XI The compound is unitary at TLC (eluent $CHCl_3:CH_3OH$ 85:15) and at HPLC.

Elemental analysis ($C_{21}H_{31}N_3O_7S$):

| | | | | |
|---|---|---|---|---|
| calc. % | C 53.72 | H 6.65 | N 8.95 | S 6.83 |
| found % | C 53.53 | H 6.70 | N 8.74 | S 6.87 |

We claim:

1. A compound of the formula

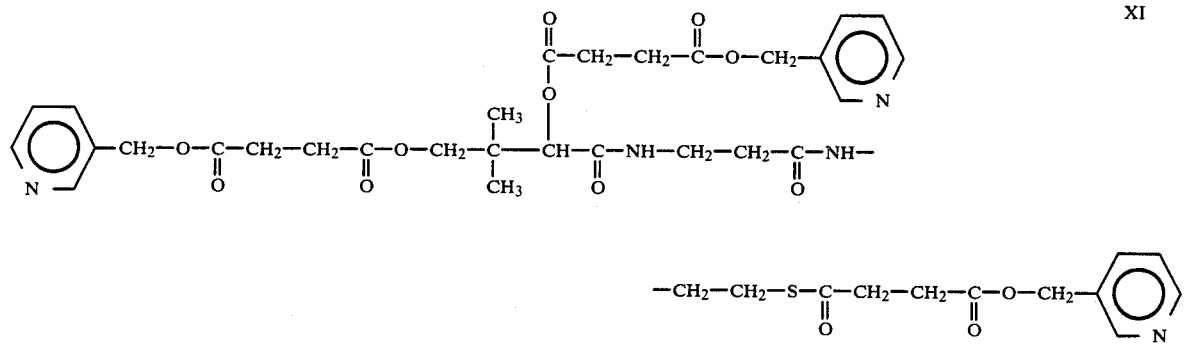

The compound is unitary at TLC (eluent $CHCl_3:CH_3OH$ 85:15) and at HPLC.

Elemental analysis ($C_{41}H_{49}N_5O_{13}S$)

| | | | | |
|---|---|---|---|---|
| calc. % | C 57.80 | H 5.85 | N 8.22 | S 3.76 |
| found % | C 57.70 | H 5.90 | N 8.14 | S 3.68 |

EXAMPLE 8

To a solution of 14.5 g of 3-(3-pyridylmethoxycarbonyl)-propionic acid (0.0695 mole), 9.39 g of 1-hydroxybenzotriazole (0.0695 mole) in 500 ml of anhydrous tetrahydrofuran, 14.35 g of dicyclohexylcarbodiimide (0.0695 mole) are added at 0° C. The mixture is stirred 1 hr at 0° C., then the precipitate is filtered off. To the filtrate 33.5 g of thallium (I) pantetheinate (0.0695 mole) are added. The mixture is stirred at room temperature for 12 hrs, the precipitate is then filtered off and washed with tetrahydrofuran. The combined organic fluids are evaporated and the residue treated with saline water and extracted with chloroform.

The chloroform layer is washed with saline water, dried over sodium sulfate and evaporated leaving an oily residue (28 g) which is eluted through a chromatographic column filled with 1.100 g of Merck silicagel 60 (70–230 mesh) with a chloroform:methanol (87:13) mixture.

After concentration under reduced pressure, 17 g (52%) of a viscous oil are obtained, of formula XII

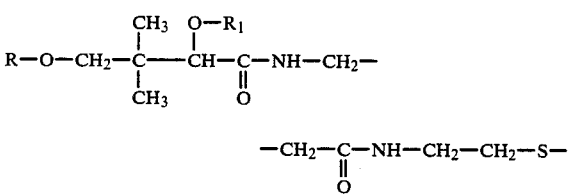

wherein R, $R_1$ and $R_2$ each represent a member of the group consisting of hydrogen, 3-pyridineacetyl and 3-(3-pyridylmethoxycarbonyl)-propionyl, with the proviso that R, $R_1$ and $R_2$ do not all simultaneously represent hydrogen; and $R_2$ may also represent a group wherein R and $R_1$ have the foregoing meaning, with the proviso that for each individual compound the meaning of R and $R_1$ is the same as in the formula I; and the non-toxic acid addition salts thereof.

2. The compound of claim 1, wherein R and $R_1$ are 3-(3-pyridylmethoxycarbonyl)-propionyl and $R_2$ is

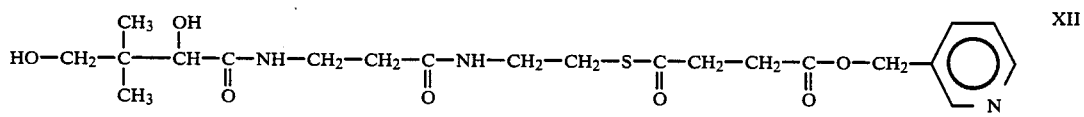

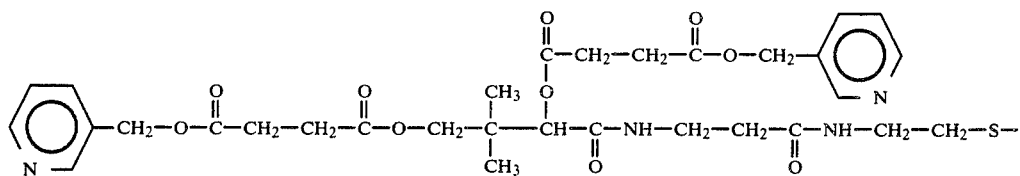

3. The compound of claim 1, wherein R and $R_1$ are 3-pyridineacetyl and $R_2$ is

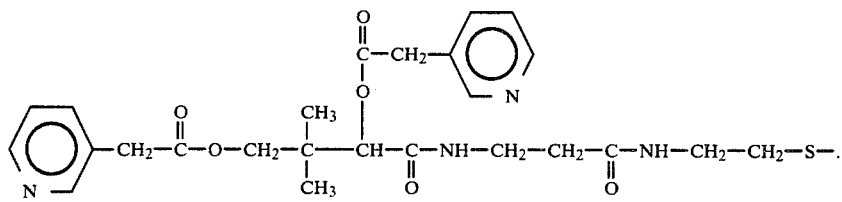

4. The compound of claim 1, wherein R, $R_1$ and $R_2$ are 3-pyridineacetyl.

5. A pharmaceutical composition in dosage unit form containing as the active ingredient the compound of claim 1.

6. A method for treating hypercholesteremia, which comprises administering orally or parenterally to a human subject the compound of claim 1 in a pharmaceutically acceptable dosage unit form, said dosage ranging between 0.05 and 2.0 grams with a daily dosage ranging between 0.1 and 10.0 g.

7. The method of claim 6, wherein the orally administered compound is in the form of a capsule tablet, powder or elixir.

8. The method of claim 7, wherein the compound is administered parenterally in the form of a solution.

* * * * *

UNITED STATES PATENT AND TRADEMARK OFFICE
CERTIFICATE OF CORRECTION

PATENT NO. : 4,571,401

DATED : February 18, 1986

INVENTOR(S) : GIAMPAOLA PICCIOLA ET AL

It is certified that error appears in the above-identified patent and that said Letters Patent is hereby corrected as shown below:

Title page, field [54], line 3 delete "PANTETHEINE" and insert therefore --PANTETHINE--

Column 1, line 3 delete "PANTETHEINE" and insert therefore --PANTETHINE--

Line 37, delete "3-pyridyneacetic" and insert therefore --3-pyridineacetic--

Column 2, line 65 delete "The" and insert therefore --Also, the--

Column 3, line 44 delete "process" and insert therefore --presence--

Column 4, Table I, first entry in the first column delete "H O" and insert therefore --$H_2O$--

Column 5, Table III, first entry in the first column, delete "H O" and insert therefore --$H_2O$--

UNITED STATES PATENT AND TRADEMARK OFFICE
CERTIFICATE OF CORRECTION

PATENT NO. : 4,571,401

DATED : February 18, 1986

INVENTOR(S) : GIAMPAOLA PICCIOLA ET AL

It is certified that error appears in the above-identified patent and that said Letters Patent is hereby corrected as shown below:

Column 6, line 55 delete "mica" and insert therefore --mice--

Signed and Sealed this

Fifth Day of August 1986

[SEAL]

Attest:

Attesting Officer

DONALD J. QUIGG

Commissioner of Patents and Trademarks